(12) United States Patent
Kijlstra et al.

(10) Patent No.: US 10,104,884 B2
(45) Date of Patent: Oct. 23, 2018

(54) INSECTICIDAL WATER-IN-OIL (W/O) FORMULATION

(71) Applicant: BAYER CROPSCIENCE AG, Monheim (DE)

(72) Inventors: Johan Kijlstra, Odenthal (DE); Francois Akle, Paris (FR); Jose Berni, Les collines d'Ugernum II (FR); Jean-Luc Heinrich, Sete (FR)

(73) Assignee: BAYER CROPSCIENCE AG, Monheim (DE)

( * ) Notice: Subject to any disclaimer, the term of this patent is extended or adjusted under 35 U.S.C. 154(b) by 0 days.

(21) Appl. No.: 14/400,574

(22) PCT Filed: May 14, 2013

(86) PCT No.: PCT/EP2013/059917
§ 371 (c)(1),
(2) Date: Nov. 12, 2014

(87) PCT Pub. No.: WO2013/171199
PCT Pub. Date: Nov. 21, 2013

(65) Prior Publication Data
US 2015/0098975 A1    Apr. 9, 2015

(30) Foreign Application Priority Data

May 16, 2012 (EP) .................... 12168250

(51) Int. Cl.
*A01N 25/04* (2006.01)
*A01N 25/34* (2006.01)
*A01N 53/00* (2006.01)

(52) U.S. Cl.
CPC ............. *A01N 25/04* (2013.01); *A01N 25/34* (2013.01); *A01N 53/00* (2013.01)

(58) Field of Classification Search
CPC ..... A01N 25/04; A01N 53/00; A01N 2300/00
See application file for complete search history.

(56) References Cited

U.S. PATENT DOCUMENTS

| 5,773,016 A * | 6/1998 | Nelson | A01N 25/04 424/405 |
| 6,294,576 B1 * | 9/2001 | Mori | C07C 69/747 424/405 |
| 2007/0191230 A1 * | 8/2007 | Pompeo | A01N 25/02 504/364 |
| 2008/0318786 A1 * | 12/2008 | Rosinger | A01N 41/10 504/139 |
| 2009/0163582 A1 * | 6/2009 | Wang | A01N 25/06 514/464 |

FOREIGN PATENT DOCUMENTS

| DE | 102006023413 A1 | 11/2007 |
| FR | 992736 A | 10/1951 |
| GB | 727577 A | 4/1955 |
| WO | 2011092722 A1 | 8/2007 |
| WO | 2007131679 A2 | 11/2007 |
| WO | WO 2007/131679 | * 11/2007 |

OTHER PUBLICATIONS

International Search Report from corresponding PCT/EP2013/059917, dated Jul. 11, 2013.

* cited by examiner

*Primary Examiner* — Anna R Falkowitz
(74) *Attorney, Agent, or Firm* — McBee Moore Woodward & Vanik IP, LLC

(57) ABSTRACT

The invention relates to an insecticidal water-in-oil (W/O) formulation with at least one insecticidal active substance and at least one burning salt and to the preparation of this formulation. The formulation according to the invention is particularly suitable for the treatment of suitable supports, in particular of paper supports, in an economical one-step process with the aid of conventional application processes. In addition, the present invention relates to insecticidal, smoulderable products which are prepared by treating a support with the formulation according to the invention.

18 Claims, 1 Drawing Sheet

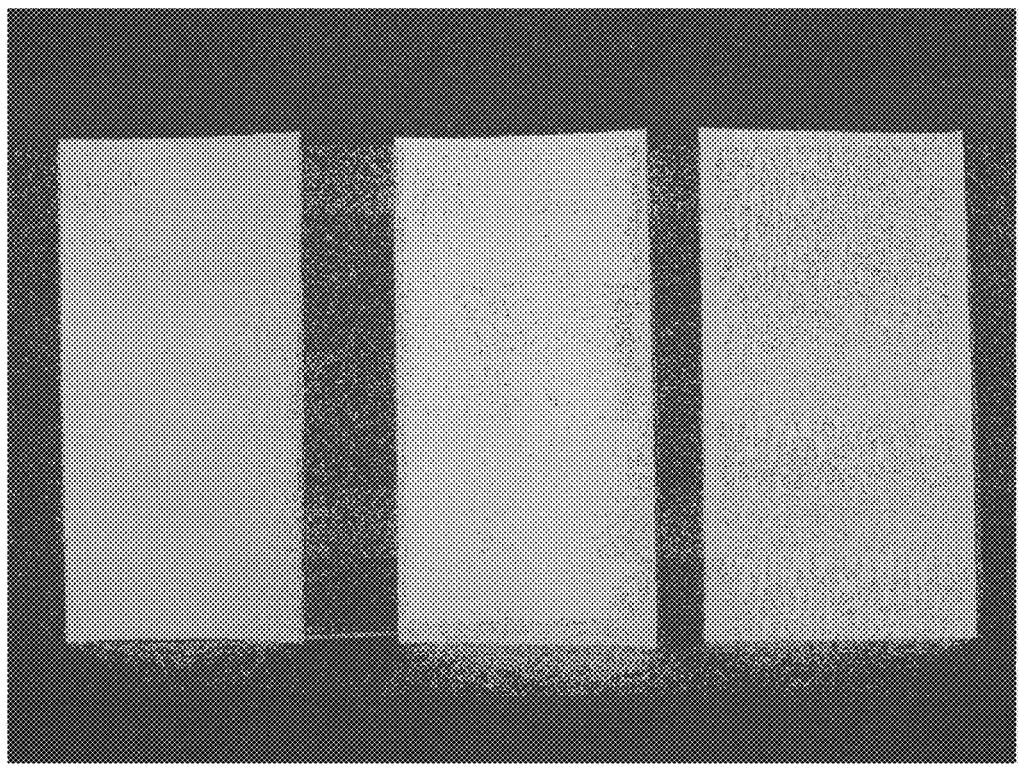

INSECTICIDAL WATER-IN-OIL (W/O) FORMULATION

CROSS REFERENCE TO RELATED APPLICATIONS

This application is a § 371 National Stage Application of PCT/EP2013/059917, filed May 14, 2013, which claims priority to EP 12168250.4, filed May 16, 2012.

BACKGROUND

Field of the Invention

The invention relates to an insecticidal water-in-oil (W/O) formulation with at least one insecticidal active substance and at least one burning salt and to the preparation of this formulation. The formulation according to the invention is particularly suitable for the treatment of suitable supports, in particular of paper supports, in an economical one-step process with the aid of conventional application processes. In addition, the present invention relates to insecticidal, smoulderable products which can be prepared by treating a support with the formulation according to the invention.

Description of Related Art

US-A-2009/0163582 describes a water-in-oil (W/O) formulation in which a polyglycerol fatty acid ester or a sorbitan fatty acid ester is employed as emulsifier, a pesticide, for example a pyrethroid, as active substance and acetyl ester, a methyl ester, an acetyl tributyl citrate, a white mineral oil or a combination of these as the solvent. This formulation takes the form of an aerosol formulation for the end user.

WO-A-2007/131679 describes a paper impregnated with an insecticidal active substance. The paper here is prepared in a two-step process in which the paper is first pretreated with an aqueous 6% strength potassium nitrate solution and then dried, and then, in a further step, impregnated with active substance solution. WO-A-2007/131679 does not disclose any formulation in which the paper can be treated in a one-step process, in particular with an insecticidal active substance and the potassium nitrate salt.

WO-A-2011/092722 describes a paper impregnated with an insecticidal active substance, which paper, again, is prepared in a two-step process. Analogously to the process of WO-A-2007/131679, the paper is first treated with a potassium nitrate before being dried and then impregnated with the active substance.

SUMMARY

The object of the present invention was to provide a formulation which is chemico-physically stable regarding an insecticidal active substance (i.e. for example a pyrethroid) and a burning salt and which is therefore suitable in particular for the treatment of a support such as, for example, a paper. Preferably, the formulation is intended to make possible the treatment of the support in an economical and industrially robust one-step process. In this one-step process, the required application weight of the formulation according to the invention is applied to the support in one process step so that the support will thereafter contain the functional formulation components such as, for example, the active substance and the burning salt in a sufficiently and homogeneously distributed manner.

The formulations described in the prior art are not suitable for achieving this object. In particular, it is not possible with these known formulations to combine, in one formulation, an insecticidal active substance together with the burning salt required and to employ the combination for the purpose according to the invention. In particular, such formulations lack sufficient chemico-physical stability (to coalescence and creaming) and lack the rheological properties which are necessary for the required purpose of the invention and/or cannot be adapted simply to traditional machinery and processes for applying the formulation to a suitable support.

Surprisingly, it has now been found that the object is achieved by a water-in-oil (W/O) formulation comprising
  a) at least one surface-active emulsifying system which has a solubility in a 16% potassium nitrate salt solution of less than 1 g/l,
  b) at least one nonaqueous solvent,
  c) at least one burning salt,
  d) at least one insecticidal active substance
  and
  e) water.

BRIEF DESCRIPTION OF THE DRAWING

FIG. 1 represents embodiments described herein.

DETAILED DESCRIPTION OF A PREFERRED EMBODIMENT

A W/O formulation generally describes a multiphase system in which an aqueous phase is dispersed in a continuous oil phase. The expression "oil" in this context is an umbrella term for water-insoluble liquids and solvents which in mixture with water or aqueous salt solutions bring about phase separation. Examples are aliphatic and aromatic solvents, vegetable and animal oils and their derivatives, fragrances or mixtures of these.

In experimental terms, one differentiates between a W/O and an O/W formulation by determining the specific conductivity. Aqueous salt solutions with a salt concentration of 5% by weight and higher will typically have a high specific conductivity in the mS/cm range, while the specific conductivity of aliphatic and aromatic solvents will typically be in the µS/cm range or below. As a consequence, a burning-salt-containing formulation will experimentally be classified as a W/O formulation when its specific conductivity amounts to less than 0.1 mS/cm. The conductivity of the present W/O formulation according to the invention is therefore preferably less than 0.1 mS/cm, measured at room temperature (20° C.).

Surface-active emulsifiers which are suitable for the W/O formulations according to the invention as the at least one surface-active emulsifying system are those which in each case have a solubility in a 16% potassium nitrate salt solution of less than 1 g/l (the solubility being determined by conventional processes at a temperature of 20° C.).

Suitable surface-active emulsifying systems which have a solubility in a 16% potassium nitrate salt solution of less than 1 g/l are, preferably, nonionic surface-active emulsifiers (also referred to as nonionic surface-active agents) with an HLB value in the range of from approximately 2 to approximately 10, preferably 2 to 10, more preferably between approximately 2 to approximately 8, preferably 2 to 8 and especially preferably between approximately 3 and approximately 6, preferably between 3 and 6. Some of the surface-active agents which can be used in accordance with the invention are listed for example in Kirk-Othmer, "Encyclopedia of Chemical Technology", $3^{rd}$ Edition, 1979, Volume 8, page 913.

The HLB value (HLB=hydrophilic-lipophilic balance) is an empiric scale defined by W. C. Griffin (J. Soc. Cosmetic Chemists, 1, 311 (1949)) which expresses the amphiphilic nature of emulsifying agents (in particular of nonionic surface-active agents). The lowest HLB values are assigned to the surface-active agents with the lowest hydrophilicity. Processes for determining the HLB are well known in the art, and any such process can be employed for determining the HLB. A description of the HLB system and processes for determining the HLB are described in "The HLB-System: a time saving guide to emulsifier selection", ICI Americas Inc., Wilmington, Del., 1976.

Nonionic surface-active emulsifiers which are suitable in accordance with the invention are especially preferably selected from the group consisting of alkylphenol ethoxylates, alkanol ethoxylates, alkylamine ethoxylates, sorbitan esters (such as the Span series) and their ethoxylates (such as the Tween series), castor oil ethoxylates, ethylene oxidepropylene oxide block copolymers, alkanolpropylene oxideethylene oxide copolymers, polyglycerols and polyglycerol esters.

The hydrophilicitylipophilicity balance (HLB) in nonionic surface-active agents may be adjusted by modifying the degree of ethoxylation.

Examples of nonionic surface-active emulsifiers for W/O formulations which can be used for the invention are (the order of the list is: brand name, HLB value, manufacturer); Brij 52 POE-(2)-cetyl alcohol; 5.3; Croda; Brij 72 POE-(2)-stearyl alcohol, 4.9, Croda; Brij 92V POE-(2)-oleyl alcohol, 4.9, Croda; Disponil TA 1.3, Cognis; Span 20, sorbitan monolaurate, 8.6, Croda; Span 40 sorbitan monopalmitate, 6.7, Croda; Span 60 sorbitan monostearate, 4.7, Croda; Span 80 sorbitan monooleate, 4.3, Croda; Span 85, sorbitan trioleate, 1.8, Croda; Hostacerin SFO, 3-4, Clariant; AGNIQUE® FOH 7OC-2 EO (Synative 3370) Cognis; Dehypon OCP 502, Cognis; Dehypon OCP 503, Cognis; AGNIQUE® FOH 90C-5, 4.9, Cognis; AGNIQUE® FOH 90C-3, 6.6, Cognis; AGNIQUE® FOH 5OC-4, 9, Cognis; Genapol O 020, 5, Clariant; Atlox 4912, 5-6; Atlox 4914, 5-7, Emulsogen V 1816, 6, Clariant; Emulsogen V 1816-1, 8, Clariant; Genapol PF 10, 2, Clariant; Genapol PF 20 P, 4, Clariant; Genapol PF 40, 6, Clariant; Genapol 2822, 6, Clariant; Genapol 3970, 3, Clariant; Agrimer AL 25, 3-5, ISP; Agrimer AL 23, 9-11, ISP; Agrimer AL 31, 7-8, ISP; Agrimer VA-3, 4-7, ISP; LAMEFORM® TGI, Cognis; Monomuls 90-O 18, Cognis; DEHYMULS® PGPH, Cognis; Hostacerin DGI, 5, Clariant; GW 1250 (HLB 5), 5, Evonik.

A surface-active emulsifying system which is suitable in accordance with the invention is also an ionic surface-active agent which has a solubility in a 16% potassium nitrate salt solution (the solubility being measured at a temperature of 20° C., using traditional processes) of less than 1 g/l.

The ionic surface-active agents for the emulsifying system are preferably selected from the group of the anionic surface-active agents consisting of alkylsulphonates, arylsulphonates, alkylarylsulphonates, aryl ether sulphonates, lignosulphonates, alkyl sulphates, alkyl ether sulphates sulphosuccinates, aliphatic and aromatic phosphate esters, alkoxylated phosphate esters, alkylcarboxylates and polycarboxylates; in each case as salts with monovalent or polyvalent cations (for example alkali metal salts, alkaline earth metal salts, ammonium salts) or together with a cationic surface-active agent (such as, for example, aliphatic primary, secondary and tertiary amines from the Armeen® series from AkzoNobel).

Anionic surface-active agents for the emulsifying system are especially preferably selected from the group consisting of aliphatic alcohol sulphates, alkylarylsulphonates or lignosulphonates; in each as salts with monovalent or polyvalent cations.

The anionic surface-active agents are in each case preferably present in the formulation according to the invention as metal salts with polyvalent cation (for example calcium salt, magnesium salt, aluminium salt and iron salt).

Salts of polyvalent cations which are preferably employed are alkaline earth metal salts, and even more preferably calcium salts.

In a further preferred embodiment of the invention, the at least one emulsifying system for W/O formulations which is employed for the formulation is selected from the group consisting of: alkylsulphonates, arylsulphonates, alkylarylsulphonates, aryl ether sulphonates, lignosulphonates, alkyl sulphates, alkyl ether sulphates, sulphosuccinates, aliphatic and aromatic phosphate esters, alkoxylated phosphate esters, alkylcarboxylates and polycarboxylates; in each case as salts of polyvalent cations, preferably alkaline earth metal salts and even more preferably calcium salts.

An example of such an emulsifying system is calcium salts of alkylarylsulphonates CALSOGEN® 4814 (Clariant) and NANSA EVM 70/2E (Huntsmann), Emulsifier 1371A (Clariant), and also for example calcium soaps, magnesium soaps and aluminium soaps of a very wide range of fatty acids (such as, for example, Liga calcium stearate CPR-5, Ligamed MF-2-V and Ligastar ALG-V from Peter Greven Fett-Chemie GmbH & Co. KG).

In a further preferred embodiment of the invention, the at least one emulsifying system for W/O formulations employed for the formulation is a nonionic surface-active agent selected from the group consisting of alkylphenol ethoxylates, alkanol ethoxylates, alkylamine ethoxylates, sorbitan esters and their ethoxylates, castor oil ethoxylates, ethylene oxidepropylene oxide block copolymers, alkanolpropylene oxideethylene oxide copolymers, polyglycerols, polyglycerol esters, or an emulsifying system selected from the group consisting of alkylsulphonates, arylsulphonates, alkylarylsulphonates, aryl ether sulphonates, lignosulphonates, alkyl sulphates, alkyl ether sulphates, sulphosuccinates, aliphatic and aromatic phosphate esters, alkoxylated phosphate esters, alkylcarboxylates and polycarboxylates; in each case as salts of polyvalent cations.

In general, the W/O formulation comprises from 0.1 to 15% by weight, preferably from 0.5 to 10% by weight, more preferably between 1.5 and 5% by weight, of at least one surface-active emulsifying system which has a solubility in a 16% potassium nitrate salt solution of less then 1 g/l.

In a preferred embodiment of the invention, the water-in-oil formulation according to the invention comprises, besides the above-described surface-active emulsifier system, additionally also at least one further additional nonionic surface-active agent, which further surface-active agent has an HLB value of in the range from approximately 8 to approximately 18, preferably 8 to 18, more preferably between approximately 10 to approximately 16, preferably 10 to 16, even more preferably between approximately 11 and approximately 16, preferably 11 to 16. Preferably, the weight fraction of this further nonionic surface-active agent is between 0.1 to 10% by weight, preferably 1 to 7% by weight, based on the W/O formulation.

Examples of second surface-active agents which can be used for the invention are (order of listing: brand name, HLB value, manufacturer): Arkopal N 040, 9, Clariant; Arkopal N 100, 13, Clariant; Arkopal N 150, 15, Clariant; Brij 30

POE-(4)-lauryl alcohol, 9.7, Croda; Brij 58 POE-(20)-cetyl alcohol, 15.7, Croda; Brij 76 POE-(10)-stearyl alcohol, 12.4, Croda; Brij 96V POE-(10)-oleyl alcohol, 12.4, Croda; Brij 98V POE-(20)-oleyl alcohol, 15.3, Croda; Lubrol 17A17 POE-(17)-oleyl alcohol, 14.9, Croda; Synperonic L11 POE-(11)-lauryl alcohol, 15, Croda; Tween 20 POE-(20)-sorbitan monolaurate 16.7; Tween 21 POE-(4)-sorbitan monolaurate, 13.3; Tween 40 POE-(20)-sorbitan monopalmitate, 15.6; Tween 60 POE-(20)-sorbitan monostearate, 14.9; Tween 65 POE-(4)-sorbitan monostearate, 9.6; Tween 65 POE-(20)-sorbitan tristearate, 10.5; Tween 80 POE-(20)-sorbitan monooleate, 15; Tween 81 POE-(5)-sorbitan monooleate, 10; Tween 85 POE-(20)-sorbitan trioleate, 11; Cremophor RH 40 polyoxyl 40 hydrogenated castor oil, 14-16, BASF; Cremophor RH 60 PEG-60 hydrogenated castor oil, 15-17, BASF; Atlox 4913, 11-12; Emulsogen V 1816-2, 12, Clariant; Genapol V 4829, 14, Clariant; Emulsogen V 2436, 11, Clariant; Emulsogen 3510, 11, Clariant.

In a further embodiment of the invention, it is preferred to add a further (third) anionic surface-active agent to the W/O formulation so as to fine-tune in particular the viscosity and foam properties of the formulation. This anionic surface-active agent is preferably present in the form of salts with monovalent cations. The weight fraction of this further anionic surface-active agent is preferably between 0 to 10% by weight, preferably 1 to 4% by weight, based on the W/O formulation.

Nonaqueous solvents which can be used for the present invention are numerous and are sparingly soluble in water. Nonaqueous solvents which are especially suitable for use in the present W/O formulation comprise aromatic hydrocarbons such as, for example, alkylbenzenes or alkylnaphthalenes (for example Solvesso 100, Solvesso 150 and Solvesso 200, Solvesso is a registered brand; xylenes; Reutasolv DI, Reutasolv MP, Reutasolv BP 4201, Reutasolv is a registered brand); aliphatic solvents (for example kerosene, Exxsol D60 and D80 from ExxonMobil), ketones (for example cyclohexanone or methlycyclohexanone); alcohols (for example benzyl alcohol, furfuryl alcohol or butanol); N-alkylpyrrolidones (for example N-methylpyrrolidone or N-octylpyrrolidone); dimethylamides of fatty acids (for example $C_8$-$C_{10}$-fatty acid dimethylamide); vegetable and animal oils and chlorinated hydrocarbons (for example chlorobenzenes).

The expression vegetable oils as used in the present context includes oils from all oil-producing plants, such as rapeseed oil, soya oil, palm oil, sunflower oil, cottonseed oil, corn oil, linseed oil, coconut oil, safflower oil or castor oil. The expression animal oil as used in the present context includes oils from oil-producing animals, such as tallow oil. Other examples of nonaqueous solvents are the transesterification products of these oils, such as alkyl esters, for example rapeseed oil methyl esters, such as Radia 7961 (Fina Chemicals, Belgium), or rapeseed oil ethyl esters. Vegetable oils are preferably esters of $C_{10}$-$C_{22}$-, preferably $C_{12}$-$C_{22}$-fatty acids. Examples of such $C_{10}$-$C_{22}$-fatty acid esters are esters of unsaturated or saturated $C_{10}$-$C_{22}$-fatty acids, in particular those with an even number of carbon atoms, such as, for example, cis-erucic acid, isoerucic acid, lauric acid, palmitic acid, myristic acid, in particular $C_{18}$-fatty acids, such as stearic acid, linoleic acid or linolenic acid. Examples of $C_{10}$-$C_{22}$-fatty acid esters are those esters which are obtainable by reacting glycerol or glycol with $C_{10}$-$C_{22}$-fatty acids and which are present for example in oils from oil-producing plants, and ($C_1$-$C_{20}$)alkyl ($C_{10}$-$C_{22}$)-fatty acid esters, which can be obtained for example by transesterifying these glycerol- or glycol-$C_{10}$-$C_{22}$-fatty acid esters with $C_1$-$C_{20}$-alcohols (such as methanol, ethanol, propanol or butanol). The transesterification can be carried out by processes generally known in the art and which are described, for example, in Römpps Chemie Lexikon, $9^{th}$ edition, volume 2, page 1343, Thieme Verlag, Stuttgart. $C_1$-$C_{20}$ Alkyl $C_1$-$C_{22}$-fatty acid esters which are preferably used are methyl esters, ethyl esters, n-propylesters, isopropylesters, n-butylesters, isobutylesters, n-pentylesters, isopentylesters, neopentylesters, n-hexylesters, isohexylesters, n-heptylesters, isoheptylesters, n-octylesters, 2-ethylhexylesters, n-nonylesters, isononylesters and dodecylesters. Glycerol and glycol $C_{10}$-$C_{22}$-fatty acid esters which are preferred are the uniform or mixed glycerol or glycol esters of $C_{10}$-$C_{22}$-fatty acids, in particular of fatty acids with an even number of carbon atoms, such as cis-erucic acid, isoerucic acid, lauric acid, palmitic acid, myristic acid, in particular of a $C_{18}$-fatty acid, such as stearic acid, linoleic acid or linolenic acid.

Nonaqueous solvents which are especially preferred in accordance with the invention are dimethylamides of fatty acids (such as, for example, Genagen), vegetable oils (such as, for example, rapeseed oil methyl esters) and alkylnaphthalenes (such as, for example, Solvesso).

In a preferred embodiment, the active substance is soluble in the selected solvent. It may be advantageous to include one or more cosolvents, in particular when the active substance is not very readily soluble in the abovementioned solvents.

According to the invention, the W/O formulation preferably comprises from 5 to 75% by weight, preferably from 15 to 55% by weight, of at least one nonaqueous solvent as component of the W/O formulation according to the invention.

A further component of the formulation according to the invention is at least one burning salt. Burning salts allow supports which are treated with the formulation according to the invention to be controlled after igniting and subsequently extinguishing the flame and to smoulder uniformly. Therefore, the burning salt is capable of ensuring the combustibility of the treated support in respect of the rate and completeness of combustion without allowing spontaneous ignition.

A burning salt is preferably selected from the group of nitrate salts (for example potassium nitrate, chromium nitrate, iron nitrate, copper nitrate, sodium nitrate). Potassium nitrate is preferably employed as the burning salt.

According to the invention, the W/O formulation preferably comprises from 6 to 25% by weight, preferably from 8 to 15% by weight, of at least one burning salt as component of the W/O formulation according to the invention.

At least one insecticidal active substance, preferably a hydrophobic insecticidal active substance, is employed in the W/O formulation according to the invention. Preferred hydrophobic insecticidal active substances are pyrethroids, bifenthrin, fipronil, a benzoylurea derivative (such as, for example, hexaflumuron, teflubenzuron, flufenoxuron), a phosphoric ester (such as, for example, phoxim, parathion, fenitrothion, trichlorphon or dichlorophos), or a carbamate (such as, for example, propoxur, pirimcarb or aldicarb). A hydrophobic insecticidal active substance which is even more preferably employed is an active substance selected from the group of the pyrethroids. Moreover, it is also possible to provide two or more insecticidal active substances together on the support, in particular the paper support, such as, for example, 2, 3, 4 or more insecticidal active substances.

Pyrethroids for the purposes of the invention are selected in particular from the group consisting of acrinathrin, allethrin, d-allethrin, d-trans-allethrin, d-cis-trans-allethrin, alphamethrin, bathrin, bifenthrin, bioallethrin, S-bioallethrin, bioallethrin-S cyclopentenyl isomer, bioethanomethrin, biopermethrin, bioresmethrin, clocythrin, chlovaporthrin, cycloprothrin, cyfluthrin, beta-cyfluthrin, cyhalothrin, gamma-cyhalothrin, lambda-cyhalothrin, cypermethrin, alpha-cypermethrin, beta-cypermethrin, cis-cypermethrin, theta-cypermethrin, zeta-cypermethrin, cyphenotrin, deltamethrin, depallethrin, empenthrin, empenthrin (1R isomer), esbiothrin, esfenvalerate, etophenprox, fenfluthrin, fenpropathrin, fenpyrithrin, fenvalerate, flubrocythrinate, flucythrinate, tau-fluvalinate, flumethrin, fubfenprox, halfenprox, imiprothrin, kadethrin, metofluthrin, neopynamin, permethrin, cis-permethrin, trans-permethrin, phenothrin, phenothrin (1R-trans isomer), d-phenothrin, prallethrin, profluthrin, protrifenbute, pynamin forte, pyresmethrin, pyrethrin, resmethrin, cis-resmethrin, RU 15525, silafluofen, tau-fluvalinate, tefluthrin, tetramethrin (phthalthrin), tetramethrin (1R isomer), terallethrin, tralomethrin, transfluthrin, ZXI 8901, pyrethrins (pyrethrum) and any mixture of the abovementioned active substances, Esbiothrin, lambda-cyhalothrin, d-allethrin, S-bioallethrin, prallethrin, metofluthrin, pyrethrum and/or transfluthrin is/are especially preferably used as the pyrethroid. Transfluthrin is very especially preferred.

According to the invention, the W/O formulation preferably comprises from 0.1 to 20% by weight, preferably from 1 to 10% by weight, of at least one insecticide as component of the W/O formulation according to the invention.

The following compounds are examples of further insecticidal active substances which can be used for the formulation according to the invention:

(1) acetylcholin esterase (AChE) inhibitors such as, for example, carbamates, for example alanycarb (II-1-1), aldicarb (II-1-2), bendiocarb (II-1-3), benfuracarb (II-1-4), butocarboxim (II-1-5), butoxycarboxim (II-1-6), carbaryl (II-1-7), carbofuran (II-1-8), carbosulphan (II-1-9), ethiofencarb (II-1-10), fenobucarb (II-1-11), formetanate (II-1-12), furathiocarb (II-1-13), isoprocarb (II-1-14), methiocarb (II-1-15), methomyl (II-1-16), metolcarb (II-1-17), oxamyl (II-1-18), pirimicarb (II-1-19), propoxur (II-1-20), thiodicarb (II-1-21), thiofanox (II-1-22), triazamate (II-1-23), trimethacarb (II-1-24), XMC (II-1-25) and xylylcarb (II-1-26); or organophosphates, for example acephate (II-1-27), azamethiphos (II-1-28), azinphos-ethyl (II-1-29), azinphos-methyl (II-1-30), cadusafos (II-1-31), chlorethoxyfos (II-1-32), chlorfenvinphos (II-1-33), chlormephos (II-1-34), chlorpyrifos (II-1-35), chlorpyrifos-methyl (II-1-36), coumaphos (II-1-37), cyanophos (II-1-38), demeton-S-methyl (II-1-39), diazinon (II-1-40), dichlorvos/DDVP (II-1-41), dicrotophos (II-1-42), dimethoate (II-1-43), dimethylvinphos (II-1-44), disulphoton (II-1-45), EPN (II-1-46), ethion (II-1-47), ethoprophos (II-1-48), famphur (II-1-49), fenamiphos (II-1-50), fenitrothion (II-1-51), fenthion (II-1-52), fosthiazate (II-1-53), heptenophos (II-1-54), imicyafos (II-1-55), isofenphos (II-1-56), isopropyl O-(methoxyaminothiophosphoryl)salicylate (II-1-57), isoxathion (II-1-58), malathion (II-1-59), mecarbam (II-1-60), methamidophos (II-1-61), methidathion (II-1-62), mevinphos (II-1-63), monocrotophos (II-1-64), naled (II-1-65), omethoate (II-1-66), oxydemeton-methyl (II-1-67), parathion (II-1-68), parathion-methyl (II-1-69), phenthoate (II-1-70), phorate (II-1-71), phosalone (II-1-72), phosmet (II-1-73), phosphamidon (II-1-74), phoxim (II-1-75), pirimiphos-methyl (II-1-76), profenofos (II-1-77), propetamphos (II-1-78), prothiofos (II-1-79), pyraclofos (II-1-80), pyridaphenthion (II-1-81), quinalphos (II-1-82), sulfotep (II-1-83), tebupirimfos (II-1-84), temephos (II-1-85), terbufos (II-1-86), tetrachlorvinphos (II-1-87), thiometon (II-1-88), triazophos (II-1-89), trichlorfon (II-1-90) and vamidothion (II-1-91).

(2) GABA-controlled chloride channel antagonists such as, for example, cyclodiene organochlorins, for example chlordane (II-2-1) and endosulfan (II-2-2); or phenylpyrazoles (fiprols), for example ethiprole (II-2-3) and fipronil (II-2-4).

(3) Sodium channel modulators voltage-dependent sodium channel blockers such as, for example, pyrethroids, for example acrinathrin (II-3-1), allethrin (II-3-2), d-cis-trans-allethrin (II-3-3), d-trans-allethrin (II-3-4), bifenthrin (II-3-5), bioallethrin (II-3-6), bioallethrin S-cyclopentenyl isomer (II-3-7), bioresmethrin (II-3-8), cycloprothrin (II-3-9), cyfluthrin (II-3-10), beta-cyfluthrin (II-3-11), cyhalothrin (II-3-12), lambda-cyhalothrin (II-3-13), gamma-cyhalothrin (II-3-14), cypermethrin (II-3-15), alpha-cypermethrin (II-3-16), beta-cypermethrin (II-3-17), theta-cypermethrin (II-3-18), zeta-cypermethrin (II-3-19), cyphenothrin [(1R)-trans isomers] (II-3-20), deltamethrin (II-3-21), empenthrin [(EZ)-(1R) isomers) (II-3-22), esfenvalerate (II-3-23), etofenprox (II-3-24), fenpropathrin (II-3-25), fenvalerate (II-3-26), flucythrinate (II-3-27), flumethrin (II-3-28), tau-fluvalinate (II-3-29), halfenprox (II-3-30), imiprothrin (II-3-31), kadethrin (II-3-32), permethrin (II-3-33), phenothrin [(1R)-trans isomer) (II-3-34), prallethrin (II-3-35), pyrethrins (pyrethrum) (II-3-36), resmethrin (II-3-37), silafluofen (II-3-38), tefluthrin (II-3-39), tetramethrin (II-3-40), tetramethrin [(1R) isomers)] (II-3-41), tralomethrin (II-3-42) and transfluthrin (II-3-43); or DDT (II-3-44); or methoxychlor (II-3-45).

(4) Nicotinergic acetylcholine receptor (nAChR) agonists such as, for example, neonicotinoids, for example acetamiprid (II-4-1), clothianidin (II-4-2), dinotefuran (II-4-3), imidacloprid (II-4-4), nitenpyram (II-4-5), thiacloprid (II-4-6) and thiamethoxam (II-4-7); or nicotin (II-4-8).

(5) Nicotinergic acetylcholine receptor (nAChR) allosteric activators such as, for example, spinosins, for example spinetoram (II-5-1) and spinosad (II-5-2).

(6) Chloride channel activators such as, for example, avermectinsmilbemycins, for example abamectin (II-6-1), emamectin benzoate (II-6-2), lepimectin (II-6-3) and milbemectin (II-6-4).

(7) Juvenile hormone mimetics such as, for example, juvenile hormone analogues, for example hydroprene (II-7-1), kinoprene (II-7-2) and methoprene (II-7-3); or fenoxycarb (II-7-4); or pyriproxyfen (II-7-5).

(8) Active substances with unknown or unspecific mechanisms of action such as, for example, alkyl halides, for example methyl bromide (II-8-1) and other alkyl halides; or chloropicrin (II-8-2); or sulphuryl fluoride (II-8-3); or borax (II-8-4); or tartar emetic (II-8-5).

(9) Selective antifeedants, for example pymetrozine (II-9-1); or flonicamid (II-9-2).

(10) Mite growth inhibitors, for example clofentezine (II-10-1), hexythiazox (II-10-2) and diflovidazin (II-10-3); or etoxazole (II-10-4).

(11) Microbial disruptors of the insect gut membrane, for example *Bacillus thuringiensis* subspecies *israelensis* (II-11-1), *Bacillus sphaericus* (II-11-2), *Bacillus thuringiensis* subspecies *aizawai* (II-11-3), *Bacillus thuringiensis* subspecies *kurstaki* (II-11-4), *Bacillus thuringiensis* subspecies *tenebrionis* (II-11-5) and BT plant proteins:

Cry1Ab, Cry1Ac, Cry1Fa, Cry2Ab, mCry3A, Cry3Ab, Cry3Bb, Cry3435Ab1 (II-11-6).

(12) Oxidative phosphorylation inhibitors, ATP disruptors, such as, for example, diafenthiuron (II-12-1); or organotin compounds, for example azocyclotin (II-12-2), cyhexatin (II-12-3) and fenbutatin oxide (II-12-4); or propargite (II-12-5); or tetradifon (II-12-6).

(13) Uncouplers of oxidative phosphorylation by disrupting the H proton gradient such as, for example, chlorfenapyr (II-13-1), DNOC (II-13-2) and sulfluramid (II-13-3).

(14) Nicotinergic acetylcholine receptor antagonists such as, for example, bensultap (II-14-1), cartap hydrochloride (II-14-2), thiocyclam (II-14-3) and thiosultap-sodium (II-14-4).

(15) Chitin biosynthesis inhibitors, Type 0, such as, for example, bistrifluoron (II-15-1), chlorfluazuron (II-15-2), diflubenzuron (II-15-3), flucycloxuron (II-15-4), flufenoxuron (II-15-5), hexaflumuron (II-15-6), lufenuron (II-15-7), novaluron (II-15-8), noviflumuron (II-15-9), teflubenzuron (II-15-10) and triflumuron (II-15-11).

(16) Chitin biosynthesis inhibitors Type 1, such as, for example, buprofezine (II-16-1).

(17) Moulting disruptors, dipteran, such as, for example cyromazine (II-17-1).

(18) Ecdysone receptor agonists such as, for example, chromafenozide (II-18-1), halofenozide (II-18-2), methoxyfenozide (II-18-3) and tebufenozide (II-18-4).

(19) Octopaminergic agonists, such as, for example, amitraz (II-19-1).

(20) Complex-III electron transport inhibitors such as, for example, hydramethylnon (II-20-1); or acequinocyl (II-20-2); or fluacrypyrim (II-20-3).

(21) Complex-I electron transport inhibitors, for example METI acaricides, for example fenazaquin (II-21-1), fenpyroximate (II-21-2), pyrimidifen (II-21-3), pyridaben (II-21-4), tebufenpyrad (II-21-5) and tolfenpyrad (II-21-6); or rotenone (derris) (II-21-7).

(22) Voltage-dependent sodium channel blockers, for example indoxacarb (II-22-1); or metaflumizone (II-22-2).

(23) Acetyl-CoA carboxylase inhibitors such as, for example tetronic and tetramic acid derivatives, for example spirodiclofen (II-23-1), spiromesifen (II-23-2) and spirotetramat (II-23-3).

(24) Complex-IV electron transport inhibitors, such as, for example, phosphines, for example aluminium phosphide (II-24-1), calcium phosphide (II-24-2), phosphine (II-24-3) and zinc phosphide (II-24-4); or cyanide (II-24-5).

(25) Complex-II electron transport inhibitors, such as, for example, cyenopyrafen (II-25-1).

(28) Ryanodin receptor effectors such as, for example, diamides, for example chlorantraniliprole (II-28-1) and flubendiamide (II-28-2).

Other active substances with unknown mechanism of action, such as, for example amidoflumet (II-29-1), azadirachtin (II-29-2), benclothiaz (II-29-3), benzoximate (II-29-4), bifenazate (II-29-5), bromopropylate (II-29-6), quinomethionate (II-29-7), cryolite (II-29-8), cyantraniliprole (cyazypyr) (II-29-9), cyflumetofen (II-29-10), dicofol (II-29-11), diflovidazin (II-29-12), fluensulphone (II-29-13), flufenerim (II-29-14), flufiprole (II-29-15), fluopyram (II-29-16), fufenozide (II-29-17), imidaclothiz (II-29-18), iprodione (II-29-19), meperfluthrin (II-29-20), pyridalyl (II-29-21), pyrifluquinazon (II-29-22), tetramethylfluthrin (II-29-23) and iodmethane (II-29-24); furthermore preparations based on *Bacillus firmus* (in particular strain CNCM I-1582, for example VOTiVO™, BioNem) (II-29-25) and the following known active compounds: 3-bromo-N-{2-bromo-4-chloro-6-[(1-cyclopropylethyl)carbamoyl]phenyl}-1-(3-chloropyridin-2-yl)-1H-pyrazole-5-carboxamide (II-29-26) (known from WO2005/077934), 4-{[(6-bromopyrid-3-yl)methyl](2-fluoroethyl)amino}furan-2(5H)-one (II-29-27) (known from WO2007/115644), 4-{[(6-fluoropyrid-3-yl)methyl](2,2-difluoroethyl)amino}furan-2(5H)-one (II-29-28) (known from WO2007/115644), 4-{[(2-chloro-1,3-thiazol-5-371)methyl](2-fluoroethyl)amino}furan-2(5H)-one (II-29-29) (known from WO2007/115644), 4-{[(6-chloropyrid-3-yl)methyl](2-fluoroethyl)amino}furan-2(5H)-one (II-29-30) (known from WO2007/115644), flupyradifurone (II-29-31), 4-{[(6-chloro-5-fluoropyrid-3-yl)methyl](methyl)amino}furan-2(5H)-one (II-29-32) (known from WO2007/115643), 4-{[(5,6-dichloropyrid-3-yl)methyl](2-fluoroethyl)amino}furan-2(5H)-one (II-29-33) (known from WO2007/115646), 4-{[(6-chloro-5-fluoropyrid-3-yl)methyl](cyclopropyl)amino}furan-2(5H)-one (II-29-34) (known from WO2007/115643), 4-{[(6-chloropyrid-3-yl)methyl](cyclopropyl)amino}furan-2(5H)-one (II-29-35) (known from EP-A-0 539 588), 4-{[(6-chloropyrid-3-yl)methyl](methyl)amino}furan-2(5H)-one (II-29-36) (known from EP-A-0 539 588), {[1-(6-chloropyridin-3-yl)ethyl](methyl)oxido-$\lambda^4$-sulphanylidene}cyanamide (II-29-37) (known from WO2007/149134) and its diastereomers {[(1R)-1-(6-chloropyridin-3-yl)ethyl](methyl)oxido-$\lambda^4$-sulphanylidene}cyanamide (A) (II-29-38) and {[(1S)-1-(6-chloropyridin-3-yl)ethyl](methyl)oxido-$\lambda^4$-sulphanylidene}cyanamide (B) (II-29-39) (also known from WO2007/149134) and sulfoxaflor (II-29-40) and its diastereomers [(R)-methyl(oxido){(1R)-1-[6-(trifluoromethyl)pyridin-3-yl]ethyl}-$\lambda^4$-sulphanylidene]cyanamide (A1) (II-29-41) and [(S)-methyl(oxido){(1S)-1-[6-(trifluoromethyl)pyridin-3-yl]ethyl}-$\lambda^4$-sulphanylidene]cyanamide (A2) (II-29-42), referred to as diastereomer group A (known from WO2010/074747, WO2010/074751), [(R)-methyl(oxido){(1S)-1-[6-(trifluoromethyl)pyridin-3-yl]ethyl}-$\lambda^4$-sulphanylidene]cyanamide (B1) (II-29-43) and [(S)-methyl(oxido){(1R)-1-[6-(trifluoromethyl)pyridin-3-yl]ethyl}-$\lambda^4$-sulphanylidene]cyanamide (B2) (II-29-44), referred to as diastereomer group B (also known from WO2010/074747, WO2010/074751) and 11-(4-chloro-2,6-dimethylphenyl)-12-hydroxy-1,4-dioxa-9-azadispiro[4.2.4.2]tetradec-11-en-10-one (II-29-45) (known from WO2006/089633), 3-(4'-fluoro-2,4-dimethylbiphenyl-3-yl)-4-hydroxy-8-oxa-1-azaspiro[4.5]dec-3-en-2-one (II-29-46) (known from WO2008/067911), 1-{2-fluoro-4-methyl-5-[(2,2,2-trifluoroethyl)sulphinyl]phenyl}-3-(trifluoromethyl)-1H-1,2,4-triazole-5-amine (II-29-47) (known from WO2006/043635), [(3S,4aR,12R,12aS,12bS)-3-[(cyclopropylcarbonyl)oxy]-6,12-dihydroxy-4,12b-dimethyl-[1-oxo-9-(pyridin-3-yl)-1,3,4,4a,5,6,6a,12,12a,12b-decahydro-2H,11H-benzo[1]pyrano[4,3-b]chromen-4-yl]methylcyclopropanecarboxylate (II-29-48) (known from WO2008/066153), 2-cyano-3-(difluoromethoxy)-N,N-dimethylbenzenesulphonamide (II-29-49) (known from WO2006/056433), 2-cyano-3-(difluoromethoxy)-N-methylbenzenesulphonamide (II-29-50) (known from WO2006/100288), 2-cyano-3-(difluoromethoxy)-N-ethylbenzenesulphonamide (II-29-51) (known from WO2005/035486), 4-(difluoromethoxy)-N-ethyl-N-methyl-1,2-benzothiazole-3-amine 1,1-dioxide (II-29-52) (known from WO2007/057407), N-[1-(2,3-dimethylphenyl)-2-(3,5-dimethylphenyl)ethyl]-4,5-dihydro-1,3-thiazole-2-amine (II-29-53) (known from WO2008/104503), {1'-[(2E)-3-(4-chlorophenyl)prop-2-en-1-yl]-5-fluorospiro[indol-3,4'-piperidine]-1(2H)-yl}(2-chloropyridin-4-yl)methanone (II-29-54) (known from WO2003/106457), 3-(2,5-dimethylphenyl)-4-hydroxy-8-methoxy-1,8-diazaspiro[4.5]dec-3-en-2-one (II-29-55) (known from WO2009/049851), 3-(2,5-dimethylphenyl)-8-methoxy-2-oxo-1,8-diazaspiro[4.5]dec-3-en-4-yl ethylcarbonate (II-29-56) (known from WO2009/049851), 4-(but-2-in-1-yloxy)-6-(3,5-dimethylpiperidin-1-yl)-5-fluoropyrimidine (II-29-57) (known from WO2004/099160), (2,2,3,3,4,4,5,5-octafluoropentyl)(3,3,3-trifluoropropyl)malononitrile (II-29-58) (known from WO2005/063094), (2,2,3,3,4,4,5,5-octafluoropentyl)(3,3,4,4,4-pentafluorobutyl)malononitrile (II-29-59) (known from WO2005/063094), 8-[2-(cyclopropylmethoxy)-4-(trifluoromethyl)phenoxy]-3-[6-(trifluoromethyl)pyridazin-3-yl]-3-azabicyclo [3.2.1]octane (II-29-60) (known from WO2007/040280), flometoquin (II-29-61), PF1364 (CAS Reg. No. 1204776-60-2) (II-29-62) (known from JP2010/018586), 5-[5-(3,5-dichlorophenyl)-5-(trifluoromethyl)-4,5-dihydro-1,2-oxazol-3-yl]-2-(1H-1,2,4-triazol-1-yl)benzonitrile (II-29-63) (known from WO2007/075459), 5-[5-(2-chloropyridin-4-yl)-5-(trifluoromethyl)-4,5-dihydro-1,2-oxazol-3-yl]-2-(1H-1,2,4-triazol-1-yl)benzonitrile (II-29-64) (known from WO2007/075459), 4-[5-(3,5-dichlorophenyl)-5-(trifluoromethyl)-4,5-dihydro-1,2-oxazol-3-yl]-2-methyl-N-{2-oxo-2-[(2,2,2-trifluoroethyl)amino]ethyl}benzamide (II-29-65) (known from WO2005/085216), 4-{[(6-chloropyridin-3-yl)methyl](cyclopropyl)amino}-1,3-oxazol-2(5H)-one (II-29-66), 4-{[(6-chloropyridin-3-yl)methyl](2,2-difluoroethyl)amino}-1,3-oxazol-2(5H)-one (II-29-67), 4-{[(6-chloropyridin-3-yl)methyl](ethyl)amino}-1,3-oxazol-2(5H)-one (II-29-68), 4-{[(6-chloropyridin-3-yl)methyl](methyl)amino}-1,3-oxazol-2(5H)-one (II-29-69) (all known from WO2010/005692), NNI-0711 (II-29-70) (known from WO2002/096882), 1-acetyl-N-[4-(1,1,1,3,3,3-hexafluoro-2-methoxypropan-2-yl)-3-isobutylphenyl]-N-isobutyryl-3,5-dimethyl-1H-pyrazole-4-carboxamide (II-29-71) (known from WO2002/096882), methyl 2-[2-({[3-bromo-1-(3-chloropyridin-2-yl)-1H-pyrazol-5-yl]carbonyl}amino)-5-chloro-3-methylbenzoyl]-2-methylhydrazinecarboxylate (II-29-72) (known from WO2005/085216), methyl 2-[2-({[3-bromo-1-(3-chloropyridin-2-yl)-1H-pyrazol-5-yl]carbonyl}amino)-5-cyano-3-methylbenzoyl]-2-ethylhydrazinecarboxylate (II-29-73) (known from WO2005/085216), methyl 2-[2-({[3-bromo-1-(3-chloropyridin-2-yl)-1H-pyrazol-5-yl]carbonyl}amino)-5-cyano-3-methylbenzoyl]-2-methylhydrazinecarboxylate (II-29-74) (known from WO2005/085216), methyl 2-[3,5-dibromo-2-({[3-bromo-1-(3-chloropyridin-2-yl)-1H-pyrazol-5-yl]carbonyl}amino)benzoyl]-1,2-diethylhydrazinecarboxylate (II-29-75) (known from WO2005/085216), methyl 2-[3,5-dibromo-2-({[3-bromo-1-(3-chloropyridin-2-yl)-1H-pyrazol-5-yl]carbonyl}amino)benzoyl]-2-ethylhydrazinecarboxylate (II-29-76) (known from WO2005/085216), (5RS,7RS;5RS,7SR)-1-(6-chloro-3-pyridylmethyl)-1,2,3,5,6,7-hexahydro-7-methyl-8-nitro-5-propoxyimidazo[1,2-a]pyridine (II-29-77) (known from WO2007/101369), 2-{6-[2-(5-fluoropyridin-3-yl)-1,3-thiazol-5-yl]pyridin-2-yl}pyrimidine (II-29-78) (known from WO2010/006713), 2-{6-[2-(pyridin-3-yl)-1,3-thiazol-5-yl]pyridin-2-yl}pyrimidine (II-29-79) (known from WO2010/006713), 1-(3-chloropyridin-2-yl)-N-[4-cyano-2-methyl-6-(methylcarbamoyl)phenyl]-3-{[5-(trifluoromethyl)-1H-tetrazol-1-yl]methyl}-1H-pyrazole-5-carboxamide (II-29-80) (known from WO2010/069502), 1-(3-chloropyridin-2-yl)-N-[4-cyano-2-methyl-6-(methylcarbamoyl)phenyl]-3-{[5-(trifluoromethyl)-2H-tetrazol-2-yl]methyl}-1H-pyrazole-5-carboxamide (II-29-81) (known from WO2010/069502), N-[2-(tert.-butylcarbamoyl)-4-cyano-6-methylphenyl]-1-(3-chloropyridin-2-yl)-3-{[5-(trifluoromethyl)-1H-tetrazol-1-yl]methyl}-1H-pyrazole-5-carboxamide (II-29-82) (known from WO2010/069502), N-[2-(tert.-butylcarbamoyl)-4-cyano-6-methylphenyl]-1-(3-chloropyridin-2-yl)-3-{[5-(trifluoromethyl)-2H-tetrazol-2-yl]methyl}-1H-pyrazole-5-carboxamide (II-29-83) (known from WO2010/069502), (1E)-N-[(6-chloropyridin-3-yl)methyl]-N'-cyano-N-(2,2-difluoroethyl)ethaneimidamide (II-29-84) (known from WO2008/009360), N-[2-(5-amino-1,3,4-thiadiazol-2-yl)-4-chloro-6-methylphenyl]-3-bromo-1-(3-chloropyridin-2-yl)-1H-pyrazole-5-carboxamide (II-29-85) (known from CN102057925) and methyl 2-[3,5-d]bromo-2-({[3-bromo-1-(3-chloropyridin-2-yl)-1H-pyrazol-5-yl]carbonyl}amino)benzoyl]-2-ethyl-1-methylhydrazinecarboxylate (II-29-86) (known from WO2011/049233).

The active substances, which are here referred to by the "common name", are known and described for example in the pesticide manual ("The Pesticide Manual" 14th Ed., British Crop Protection Council 2006) or can be found on the internet (for example http://www.alanwood.net/pesticides).

The present W/O formulation comprises water as additional component. The W/O formulation according to the invention preferably comprises from 20 to 85% by weight, more preferably from 35 to 60% by weight, of water.

In a preferred embodiment of the present invention, the W/O formulation according to the invention furthermore preferably comprises at least one colorant and/or at least one fragrance. Preferably, the formulation according to the invention comprises at least one colorant and at least one fragrance.

Colorants which can be employed are inorganic pigments, for example iron oxide, titanium oxide, Prussion Blue, organic pigments and dyes such as triphenylmethanes, diphenylmethanes, oxazines, xanthenes, iminonaphthoquinones, azomethines and anthraquinones, such as, for example, Oil Yellow #101, Oil Yellow #103, Oil Pink #312, Oil Red, Oil Green BG, Oil Blue BOS, Oil Blue #603, Oil Black BY, Oil Black BS, Oil Black T-505 (Orient Kagaku Kogyo), Victoria Purc Blue BOH (Hodogaya Kagaku), Patent Pure Blue (Sumitomo Mikuni Kagaku), Crystal Violet (CI 4255) Methyl Violet (CI 42535), Ethyl Violet, Rhodamin B (CI 145170B), Malchit Green (CI 142000). Methylene Blue (CI 52015), Brilliant Blue, Methyl Green, Erythrocin B, Basic Fuchsin, m-Cresol Purple, auramin, 4-p-diethylaminophenyliminaphthoquinone, leucobasis dyes and primary or secondary acrylamine dyes such as, for example, triphenylamine, diphenylamine, o-chloroaniline, 1,2,3,-triphenylganidine, naphthylamine, diaminodiphenylmethane, p,p'-bis-dimethylaminodiphenylamine, 1,2-dianilinoethylene, p,p',p"-tris-dimethylaminotriphenylmethane, p,p'-bis-dimethylaminodiphenylmethylimine, p,p,p"-triamino-o-methyltriphenylmethane, p,p'-bis-dimethylaminodiphenyl-4-anilinonaphthylmethane, p,p',p"-triaminotriphenylmethane and the like.

It is preferred to employ anionic, cationic or basic colorants such as, for example, xanthene dyes Ceravon Fast Rhodamine B 400% (DixonChew) and Sanolin Rhodamin B02 (Clariant), the substantive dyestuff Levacell Violett BB fl. 40% (Lanxess), the azo dyestuff Bayscript Magenta LB fl. (Lanxess), Ceracryl Magenta (DixonChew), Astra Red Violett 3RC liq. (Lanxess), Astra Phloxin G (Lanxess) and Cartazine Violet 4EK liq. (Clariant).

It is especially preferred to use anionic colorants such as, for example, the xanthene dyes Ceravon Fast Rhodamine B 400% (DixonChew) and Sanolin Rhodamine B02 (Clariant), the substantive dyestuff Levacell Violett BB fl. 40% (Lanxess) and the azo dyestuff Bayscript Magenta LB fl. (Lanxess).

Depending on the solubility of the colorants, further surface-active substances are employed in accordance with the invention so as to dissolve the colorants. If, for example, a triaminotriphenylmethane is employed, the colorant is dissolved using water and a surface-active substance, preferably at elevated temperatures (up to 70° C.), before it is added to the formulation according to the invention. A suitable surface-active substance is, for example, a nonionic surface-active agent of ethoxylated alcohol (as described further above).

Natural fragrances can be selected for example from the group consisting of lavender, musk, civet, ambergris, castereum and similar fragrances: ajowan oil, almond oil, ambrette seed absolute, angelica root oil, anisole, basil oil, bay oil, benzoin resinoid, essence of bergamot, birch oil, rosewood oil, ferula oil, cajeput oil, cananga oil, *capsicum* oil, caraway oil, cardamom oil, carrot seed oil, *cassia* oil, cedar wood oil, celery seed oil, cinnamon bark oil, citronella oil, clary sage oil, clove oil, cognac oil, coriander oil, oil of cubebs, camphor oil, dill oil, tarragon oil, eucalyptus oil, fennel oil sweet, calbanum resinoid, garlic oil, geranium oil, ginger oil, grapefruit oil, hop oil, hyacinth absolute, jasmine absolute, juniper berry oil, labdanum resinoid, lavender oil, bay leaf oil, lemon oil, lemon grass oil, lavage oil, mace oil, tangerine oil, Nfisoma absolute, myrrh absolute, mustard oil, narcissus absolute, neroli oil, nutmeg oil, oak moss absolute, olibanum resinoid, onion oil, opoponax resinoid, orange oil, orange flower oil, iris concrete, pepper oil, peppermint oil, balsam of Peru, petitgrain oil, pine needle oil, rose absolute, rose oil, rosemary oil, sandalwood oil, sage oil, curly-mint oil, *styrax* oil, thyme oil, tolu balsam, tonka bean absolute, tuberose absolute, oil of turpentine, vanilla pod absolute, vetiver oil, violet leaf absolute, ylang-ylang oil and similar plant oils and the like and their mixtures.

Synthetic fragrances which may be added to the formulation according to the invention are: pinene, limonene and similar hydrocarbons, 3,3,5-trimethylcyclohexanol, linalool, geraniol, nerol, citronellol, menthol, borneol, borneylmethoxycyclohexanol, benzyl alcohol, anisyl alcohol, cinnamyl alcohol, β-phenylethyl alcohol, cis-3-hexanol, terpineol and similar alcohols; anethols, musk xylene, isoeugenol, methyleugenol and similar phenols; amylcinnamaldehyde, anisaldehyde, n-butyraldehyde, cuminaldehyde, cyclamenaldehyde, decylaldehyde, isobutyraldehyde, hexylaldehyde, heptylaldehyde, n-nonylaldehyde nonadienol, citral, citronellal, hydroxycitronellal, benzaldehyde, methylnonyl acetaldehyde, cinnamaldehyde, dodecanol, hexylcinnamaldehyde, undecanal, heliotropin, vanillin, ethylvanillin and similar aldehydes, methyl amyl ketone, methyl β-naphthyl ketone, methyl nonyl ketone, musk ketone, diacetyl, acetylpropionyl, acetylbutyryl, carvone, methone, camphor, acetophenone, p-methylacetophenone, ionone, methylionone and similar ketones; amyl butyrolactone, diphenyl oxide, methyl phenylglycidate, nonylacetone, coumarin, cineol, ethyl methylphenylglycidate and similar lactones or oxides, methylformate, isopropyl formate, linalyl formate, ethyl acetate, octyl acetate, methyl acetate, benzyl acetate, cinnamyl acetate, butyl propionate, isoamyl acetate, isopropyl isobutyrate, geranyl isovalerate, allyl capronate, butyl heptylate, octyl caprylate, methyl heptinecarboxylate, methyl octinecarboxylate, isoamyl caprylate, methyl laurate, ethyl myristate, methyl myristate, ethyl benzoate, benzyl benzoate, methyl carbinylphenylacetate, isobutyl phenylacetate, methyl cinnamate, styracin, methyl salicylate, ethyl anisate, methyl anthranilate, ethyl pyruvate, ethyl butylbutyrate, benzyl propionate, butyl acetate, butyl butyrate, p-tert-butylcyclohexyl acetate, cedryl acetate, citronellyl acetate, citronellyl formate, p-cresyl acetate, ethyl butyrate, ethyl caproate, ethyl cinnamate, ethyl phenylacetate, ethylene brassylate, geranyl acetate, geranyl formate, isoamyl salicylate, isoamyl valerate, isobornyl acetate, linalyl acetate, methyl anthranilate, methyl dihydrojasmonate, nonyl acetate, β-phenylethyl acetate, trichloromethylenephenylcarbinyl acetate, terpinyl acetate, vetiveryl acetate and similar esters. These fragrances can be used individually, or at least two of these can be used as a mixture with one another. In addition to the fragrance, the formulation according to the invention may, if appropriate, additionally contain the additives conventionally used in the fragrance industry, such as Patchouli oil or similar volatilization-inhibitory agents such as eugenol or similar viscosity-regulating agents.

The formulations according to the invention may also contain deodorizing agents such as, for example, lauryl methacrylate, geranyl crotonate, acetophenone myristate, p-methylacetophenone benzaldehyde, benzyl acetate, benzyl propionate, amylcinnamaldehyde, anisaldehyde, diphenyl oxide, methyl benzoate, ethyl benzoate, methyl phenyl acetate, ethyl phenyl acetate, neolin, safrol and the like.

The fragrances are preferably already a component of the nonaqueous solvent.

In general, the W/O formulation preferably comprises from 1 to 75% by weight, more preferably from 2 to 55% by weight, of a fragrance, even more preferably in an amount of from 5 to 15% by weight.

As a further preferred embodiment of the invention, the W/O formulation preferably comprises from 0.01 to 5% by weight, more preferably from 0.01 to 1% by weight, of a colorant. All percentages by weight which refer to the W/O formulation of the above-described components give not more than 100% in total.

If desired, the W/O formulation according to the invention furthermore comprises additives or adjuvants, preferably antifreeze agents, bittering agents, stabilizers, antifoam agents, wetters, antifoams and preservatives. Examples of suitable antifreeze agents are ethylene glycol, monopropylene glycol, glycerol, hexylene glycol, 1-methoxy-2-propanol, cyclohexanol, in particular monopropylene glycol. Bittering agents which are suitable are in particular aroma oils, preferably peppermint oil, eucalyptus oil, bitter almond oil, menthol, fruit aroma substances, preferably aroma substances of lemons, oranges, citron, grapefruit or mixtures of these, and/or denatonium benzoate. Stabilizers which may optionally be added to the formulation are acids, preferably organic acids such as dodecylbenzenesulphonic acid, acetic acid, propionic acid or citric acid, in particular citric acid, and antioxidants such as butylhydroxytoluene (BHT), butylhydroxyanisol (BHA), in particular butylhydroxytoluene. Preferred antifoam agents and defoamers are silicone-based, especially preferred are an aqueous emulsion of dialkylpolysiloxanes, commercially available as Rhodorsil®; 426R from Rhodia Chimie France, Wacker SE series from Wacker, Germany, and a mixture of dialkylpolysiloxanes as an oil, commercially available as Rhodorsil®; 416 from Rhodia Chimie, France, Wacker 5184 or Wacker SL from Wacker, Germany.

The formulations according to the invention optionally also comprise further functional additives which effect the combustion properties or other properties of supports which are treated with the formulation according to the invention. Examples of such additives which may be mentioned are phosphate salts (such as, for example, sodium phosphates, monoammonium phosphates), organic acids (for example trisodium citrate, tripotassium citrate, sodium acetate, sodium tartrate, succinic acid, malonic acid and the like) and waxes. Further examples of such additives are mineral inorganic substances such as titanium dioxide, calcium carbonate, phyllosilicates such as kaolin, and organic fillers such as microcrystalline cellulose.

A further subject matter of the invention relates to the use of a formulation according to the invention for treating a support.

According to the invention "treating" refers to a process in which a support is brought into contact with the formulation. A suitable treatment method is impregnation, for example by spraying the support with the formulation according to the invention, followed by drying, for example in the air, or immersing the support in the formulation according to the invention, followed by drying, for example in the air. Other suitable impregnation processes are impregnation by means of a pipette. A further suitable and preferred treatment process which is particularly suitable is to print the support with the formulation according to the invention.

To print the support with the formulation, it is preferred to employ established application processes or coating facilities for continuous operation. Suitable printing processes and corresponding facilities are known for example from the graphics industry (direct and indirect printing processes) and from the paper industry (coating and impregnation processes). Other known facilities/processes are the blade-coating press, the film press, the size press, the curtain coating process and others.

Especially preferred are gravure processes, where the formulation according to the invention is applied directly from the rotating engraved cylinder to the support.

It has emerged that the present application is particularly suitable for being applied homogeneously to a support by means of a gravure process. Here, the formulations according to the invention remain physically stable and can be adapted readily to the selected gravure process in respect of the rheological properties (in particular viscosity and wetting properties). In the context of the present invention, the expression "physically stable" means that in a relevant time scale for the application of the formulation in a one-step coating process, in particular by means of a gravure process, no significant or macroscopic phase separation of the water phase and the oil phase, or creaming, takes place.

Under certain circumstances, it may be necessary to adapt the viscosity of the formulation to the coating process so as to avoid undesired side-effects caused by the process (such as, for example, inhomogeneous film splitting and misting, which may result in inhomogenities in the coating). In this respect, the viscosity properties are preferably controlled via altering the weight fractions of the surface-active emulsifying system and/or via altering the composition of the surface-active emulsifying system and/or via modifying the proportions of the aqueous phase relative to the continuous "oil phase".

It has emerged that, when using a traditional gravure process and the preferred paper support defined hereinbelow, a Bingham viscosity of the W/O formulation according to the invention of between 20 and 200, preferably 30 to 150, mPa·s at 20° C. is advantageous.

The determination of the Bingham viscosity is based on measuring the shear stress at an increasing shear rate. The resulting shear stress values [Pa] are plotted versus the shear rate [$s^{-1}$]. The Bingham viscosity at higher shear rates is derived as the slope of the regression line.

The viscosity is measured at a temperature of 20° C. using a rotary viscometer using measuring systems of the cylinder type (also referred to as double gap systems) standardized as specified in DIN EN ISO 321, whose shear rate can be adjusted in a defined manner, for example from Haake, Bohlin, Mettler, Contraves and others. The viscometer should make possible measurements in a shear rate range of from 0.1 to 1200 $s^{-1}$.

An advantage of the W/O formulations according to the invention is that the Bingham viscosity can be adjusted without employing polymeric thickeners and that, therefore, a very good and homogeneous transfer of the formulation from the engraved cylinder to the support can be ensured, even with increased production speed. Formulation residues which have dried on the engraved cylinder can be removed readily with water or with customary aqueous cleaners, in contrast to formulations with polymeric thickeners.

Supports which are suitable in accordance with the invention are in particular solid combustible materials such as cellulose materials, textile materials, plastic materials and the like. Cellulose-based supports are, for example, paper, board, wood, wood chippings, wood chips or sawdust, rice husks, maize cob spindles (preferably without kernels), pecan nut shells and peanut shells. Thin particle board is also suitable as the support. A suitable cellulose-based support is described, for example, in German patent application DE 43 223 76 A1, the disclosure of which is hereby included by reference.

Supports made of textile materials are, for example, synthetic polyester or nylon fibres or natural fibres such as cotton, viscose, a linen-viscose mixture or a mixture of synthetic and natural fibres such as cellulose-polyester (synthetic paper) or cotton-polyester. Other examples are wool feltine and Trevira satin.

Supports made of polymer materials are, for example, polycarbonates, polyesters, polyamides and polyterephthalates.

Especially preferred within the scope of the present invention is the use of a cellulose-based support, in particular a paper support.

In principle, no special limitations are imposed on the paper support used here, as long as it is generally suitable for taking up at least one insecticidal active substance in question and, after igniting and extinguishing the paper support, releasing the at least one insecticidal active substance without essentially decomposing it.

However, it has emerged that paper supports with a paper weight of preferably from 25 to 300 g/m$^2$, in particular 25 to 270 g/m$^2$, especially preferably 25 to 250 g/m$^2$, very especially preferably 25 to 230 g/m$^2$, further very especially preferably 25 to 215 g/m$^2$, specifically 25 to 200 g/m$^2$, are especially suited to the purpose according to the invention.

Furthermore, it is preferred for the thickness of the paper support to be in a range of from 0.05 to 0.50 mm, especially preferably 0.07 to 0.40 mm, very especially preferably 0.08 to 0.35, furthermore very especially preferably between 0.08 and 0.25 mm, specifically 0.08 to 0.20 mm Suitable supports and processes of treating the supports are likewise described in the laid-open specification WO2007/131679A2.

Another subject matter of the present invention relates to the use of the water-in-oil formulation according to the invention for treating a support. The "treating" is preferably effected by printing the support. Even more preferably, the printing of the support is effected via a gravure process, preferably by a "one-step" printing process.

A further subject of the present invention relates to a support which has been treated with a water-in-oil formulation according to the invention.

It is preferred for the application weight of the (W/O) formulation on the support (preferably the paper support) to be in a range of from 5 to 30 ml/m$^2$, especially preferably from 12 to 22 ml/m$^2$ and very especially preferably from 15 to 20 ml/m$^2$.

The content of insecticidal active substance on a support according to the invention, in particular a paper support, is preferably between 0.05 to 5.0% by weight, more preferably between 0.1 to 2.5% by weight and even more preferably between 0.2 and 1.5% by weight.

It is preferred for the burning salt content of the treated support (preferably a paper support) to be in the range of from 0.1 to 6% by weight, especially preferably from 1 to 5% by weight and very especially preferably from 1.5 to 3% by weight.

In general, the support according to the invention (in particular a paper support) preferably comprises from 0.01 to 10% by weight, more preferably from 0.05 to 5% by weight, especially preferably from 0.1 to 2% by weight, of at least one above-described surface-active emulsifier system.

It is preferred for the treated support to comprise a fragrance which has a positive effect on the odour of the smoulderable end product before and after smouldering.

It is preferred for the fragrance content of the treated support (preferably a paper support) to be in the range of from 0.1 to 10% by weight, especially preferably from 0.5 to 5% by weight and very especially preferably from 1.0 to 3% by weight.

In a preferred embodiment of the invention, the support according to the invention (preferably a paper support) comprises, besides the above-described surface-active emulsifier system, additionally at least one other, further nonionic surface-active agent, which further surface-active agent has an HLB value in the range of from approximately 8 to approximately 18, preferably 8 to 18, more preferably between approximately 10 to approximately 16, preferably 10 to 16, even more preferably between approximately 11 to approximately 16, preferably 11 to 16. Preferably the weight fraction of this further nonionic surface-active agent amounts to between 0.1 to 4% by weight, preferably 0.3 to 1.5% by weight, based on the support according to the invention.

In a further preferred embodiment of the invention, the support according to the invention (preferably a paper support) additionally comprises a further (third) anionic surface-active agent. The weight fraction of this further anionic surface-active agent is preferably between 0 to 5% by weight, preferably 0.1 to 2.5% by weight, based on the support according to the invention. The remaining percentages by weight, which add up to not more than 100%, relate to the support (preferably to a paper support) itself.

A further subject matter of the invention relates to a process of preparing the water-in-oil formulation according to the invention, comprising the following steps:

a) dissolving at least one burning salt in water,
b) dissolving, in at least one nonaqueous solvent, at least one insecticidal active substance and at least one emulsifying system which has a solubility in a 16% potassium nitrate salt solution of less than 1 g/l,
c) mixing of the solution of step b) with the solution of step a).

If optionally further water-soluble formulation components (such as, for example, cationic or anionic colorants, further additives) are to become a component of the W/O formulation, they are added to the water in step a), together with the burning salt.

If optionally further water-insoluble liquid formulation components (such as, for example, fragrances, further additives) are to become a component of the W/O formulation, then they are admixed to the nonaqueous solvent before step b).

Mixing in step c) to give a W/O formulation according to the invention is performed by homogenizing via simple stirring or via a conventional emulsifying process.

A further subject matter of the present invention relates to an insecticidal, smoulderable product comprising an above-described support and the components of the above-described water-in-oil formulation according to the invention, where the nonaqueous solvent can evaporate from the support during the preparation (for example during a drying step which follows the preparation or at a later point in time).

A further subject matter of the invention is a process of preparing an insecticidal smoulderable product, characterized in that a support is treated with a water-in-oil formulation according to the invention. Preferably, the preparation is carried out by printing the support with the water-in-oil formulation according to the invention. More preferably, printing of the support is performed via a gravure process, preferably by a "one-step" printing process.

EXAMPLES

Example 1

Description of the Preparation of the Formulations According to the Invention

In accordance with the above-specified preparation protocol (see page 21), the following formulations according to the invention were made up with transfluthrin (Fl A=formulation A according to the invention; Fl B=formulation B according to the invention; Fl C=noninventive formulation C as comparison):

TABLE 1

Specification of the formulation components in percent by weight, based on the respective W/O formulations according to the invention (Fl A = formulation A according to the invention; Fl B = formulation B according to the invention).

| Composition | Formulation | |
| --- | --- | --- |
| | Fl A<br>% by weight | Fl B<br>% by weight |
| Transfluthrin, technical grade | 3.30 | 3.30 |
| OM 2044 (fragrance, IFF Inc.) | 9.60 | 9.60 |
| Solvesso 100 | 12.50 | 12.50 |
| Span 80 | 7.65 | 5.70 |
| Tween 80 | 0 | 1.95 |
| Potassium nitrate | 12.50 | 12.50 |
| Water | 54.45 | 54.45 |
| Total | 100.00 | 100.00 |

For comparison purposes, the following noninventive formulation was also made up with transfluthrin, proceeding as specified in the preparation protocol mentioned above:

TABLE 2

Noninventive formulation C (Fl C) for comparison.

| Composition | Formulation Fl C % by weight |
|---|---|
| Transfluthrin, technical grade | 3.30 |
| OM 2044 (fragrance, IFF Inc.) | 9.60 |
| Solvesso 100 | 12.50 |
| Span 80 | 0 |
| Tween 80 | 7.65 |
| Potassium nitrate | 12.50 |
| Water | 54.45 |
| Total | 100.00 |

Mixing of the formulations as specified in preparation step c) (see page 21) was carried out by simple stirring with the aid of a conventional magnetic stirrer.

The specific conductivity was characterized with the aid of a laboratory apparatus from Knick (Portamess® 911 Cond in combination with conductivity sensor SE 204). The Bingham viscosity of the homogenized formulations was determined using a rheometer from Haake (Haake RS-150, Sensor Z20 Din Ti) at 20° C. The results of the two measurements are shown in Table 3 which follows:

TABLE 3

Bingham viscosity and specific conductivity of the formulations prepared in accordance with Example 1.

| | Formulation | | |
|---|---|---|---|
| | Fl A | Fl B | Fl C |
| Bingham viscosity (mPa.s) | 37 | 65 | 12 |
| Specific conductivity | 0.6 µS/cm | 1.5 µS/cm | 59.4 mS/cm |
| Emulsion type | W/O | W/O | O/W |

Example 2

Description of the Preparation of the Insecticidal Smoulderable Product According to the Invention To prepare the insecticidal papers, the active substance formulations described in Example 1 (Fl A, Fl B and Fl C as control), were applied homogeneously to the entire surface of the support at a defined application weight, using a gravure process. The support employed was the offset paper Tauro Offset 90 gm (Robert Horn Group). The formulations were applied in one step using the printability tester PhantomQD™ Proofer (HARPER Graphics GmbH) and the screen roll 306 140 100 20.0C (theoretical scoop volume approximately 31 cm³ m² and engraving angle of 60 degrees, HARPER Graphics GmbH). The formulation was transferred directly from the engraved cylinder to a paper strip at constant pressure and an application weight of approximately 16 g/m². The printed paper strips were dried in ambient air for at least one hour and then tested for printing quality (via visual assessment of the homogeneity of the inking of the paper) and the smouldering behaviour.

The smouldering behaviour was checked by folding the coated paper strips lengthwise, igniting them on one side, blowing out the resulting flame and placing them onto a fireproof support so that it can smoulder away completely. The degree to which the paper strip smoulders away or carbonizes is considered to be a measure for the smouldering behaviour of the coated paper strip.

TABLE 4

Quality of the coating and smouldering behaviour of the insecticidal smoulderable products prepared in accordance with Example 2.

Insecticidal smoulderable product

| | Formulation applied | | |
|---|---|---|---|
| | Fl A | Fl B | Fl C |
| Application weight (g/m²) | 16 | 16 | 16 |
| Quality of the coating | Homogeneous | homogeneous | Inhomogeneous |
| Smouldering behaviour | Complete | complete | Incomplete |

FIG. 1 shows the quality of the coating of the insecticidal smoulderable products prepared in accordance with Example 2 (applied formulations, left to right: Fl A, Fl B and Fl C). While Fl A and Fl B show a homogeneous coating, an inhomogeneous coating is discernible in Fl C.

Example 3

Description of the Preparation of a Formulation According to the Invention without Fragrance and of an Insecticidal Smoulderable Product Analogously to Example 1, the following formulation D according to the invention (FL D) was made up with transfluthrin and without fragrance, following the above-specified preparation protocol (see page 21).

| Composition | Formulation Fl D % by weight |
|---|---|
| Transfluthrin, technical grade | 3.30 |
| Solvesso 100 | 20.00 |
| Span 80 | 5.70 |
| Tween 80 | 1.95 |
| Potassium nitrate | 12.50 |
| Water | 56.55 |
| Total | 100.00 |

Formulation D was employed analogously to Example 2 for the preparation of an insecticidal paper. The formulations were applied in one step using the printability tester PhantomQD™ Proofer (HARPER Graphics GmbH) and the screen roll 306 140 100 20.0C (theoretical scoop volume approximately 31 cm³/m² and engraving angle of 60 degrees, HARPER Graphics GmbH) to the offset paper Tauro Offset 90 gm (Robert Horn Group). The W/O formulation having a specific conductivity of <0.1 mS/cm was transferred directly from the engraved cylinder to a paper strip at constant pressure and an application weight of effectively approximately 16 g/m². Once the paper had subsequently dried in the ambient air, a homogenously inked insecticidal paper was obtained. The insecticidal paper smouldered away completely.

The invention claimed is:

1. A chemico-physically stable water-in-oil formulation comprising in admixture
   a) at least one surface-active emulsifying system which has a solubility in a 16% potassium nitrate salt solution of less than 1 g/l, b) at least one nonaqueous solvent,
c) at least one burning salt,
d) at least one insecticidal active substance which is a pyrethroid,
and
e) water,
wherein the formulation does not comprise a herbicide,
and wherein the at least one surface-active emulsifying system comprises a first nonionic surface-active agent with an HLB value in a range from 3 to 6, and
wherein the at least one surface-active emulsifying system comprises a second nonionic surface-active agent, which surface-active agent has an HLB value in a range from 11 to 16
and wherein the formulation comprises 0.5 to 10% by weight of the surface-active emulsifying system, 5 to 75% by weight of the nonaqueous solvent, 6 to 25% of the burning salt, 0.1 to 20% by weight of the insecticidal active substance, and 20 to 85% by weight water.

2. The water-in-oil formulation according to claim 1, wherein the nonionic surface-active agent with an HLB value in a range from 3 to 6 is selected from the group consisting of: alkylphenol ethoxylates, alkanol ethoxylates, alkylamine ethoxylates, sorbitan esters and their ethoxylates, castor oil ethoxylates, ethylene oxide/propylene oxide block copolymers, alkanol/propylene oxide/ethylene oxide copolymers, polyglycerols, and polyglycerol esters.

3. The water-in-oil formulation according to claim 1, wherein the burning salt is potassium nitrate.

4. The water-in-oil formulation according to claim 1, wherein the formulation additionally comprises at least one colorant and/or at least one fragrance.

5. The water-in-oil formulation according to claim 1, capable of being used for treating a support.

6. A support which has been treated with a water-in-oil formulation according to claim 1.

7. A support according to claim 6, wherein the support is a paper support.

8. A process for preparing a water-in-oil formulation according to claim 1, comprising:
a) dissolving the at least one burning salt in water,
b) dissolving, in the at least one nonaqueous solvent, the at least one insecticidal active substance and the at least one emulsifying system which has a solubility in a 16% potassium nitrate salt solution of less than 1 g/l, and
c) mixing of the solution of b) with the solution of a).

9. An insecticidal, smoulderable product, comprising
a) a support,
b) at least one emulsifying system which in each case has a solubility in a 16% potassium nitrate salt solution of less than 1 g/l,
c) at least one burning salt,
d) at least one insecticidal active substance which is a pyrethroid,
and
d) water, wherein the product does not comprise a herbicide
wherein the at least one emulsifying system comprises a nonionic surface-active agent with an HLB value in a range from 3 to 6 and
wherein the at least one emulsifying system comprises at least one further additional nonionic surface-active agent, which surface-active agent has an HLB value in a range from 11 to 16.

10. A process for preparing a support according to claim 6, comprising treating the support with the water-in-oil formulation.

11. (Withdrawn/ Previously Presented) The process according to claim 10, wherein the support is printed with the water-in-oil formulation in a one-step process.

12. The process according to claim 11, wherein the support is printed with the water-in-oil formulation by a gravure process in a one-step process.

13. The product according to claim 9, wherein the burning salt comprises potassium nitrate.

14. The formulation according to claim 1, wherein the insecticidal active substance is transfluthrin.

15. The product according to claim 9, wherein the insecticidal active substance is transfluthrin.

16. The formulation according to claim 1, comprising 1.5 to 10% by weight of the surface-active emulsifying system, 5 to 55% by weight of the nonaqueous solvent, 8 to 15% of the burning salt, 1 to 10% by weight of the insecticidal active substance, and 35 to 60% by weight water.

17. The formulation according to claim 16, comprising 1 to 7% by weight based of the formulation of the second nonionic surface-active agent.

18. The formulation according to claim 17, wherein the insecticidal active substance is transfluthrin and the burning salt is potassium nitrate.

* * * * *